Figure 1:
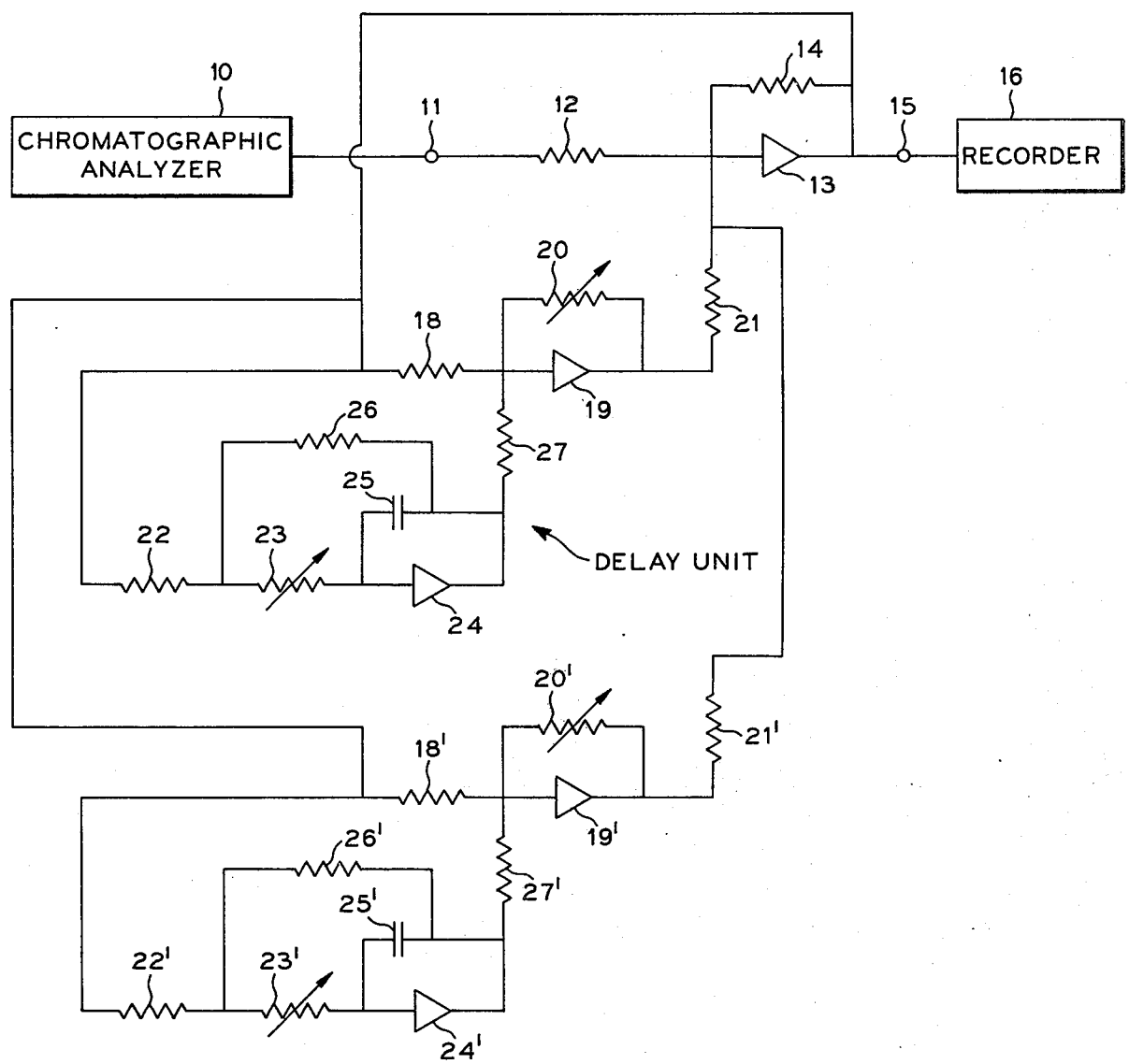

United States Patent [19]
DeFord

[11] 3,978,415
[45] Aug. 31, 1976

[54] CHROMATOGRAPHIC ANALYZER SIGNAL RESOLUTION

[75] Inventor: Donald D. DeFord, Glenview, Ill.

[73] Assignee: Phillips Petroleum Company, Bartlesville, Okla.

[22] Filed: Sept. 23, 1974

[21] Appl. No.: 508,622

[52] U.S. Cl.................................. 328/165; 73/23.1; 307/229; 328/162
[51] Int. Cl.² ..................... H04B 1/04; G01N 31/08
[58] Field of Search ............ 328/55, 162, 165, 127, 328/58; 73/23.1, 300; 307/229

[56] References Cited
UNITED STATES PATENTS

| | | |
|---|---|---|
| 3,072,855 | 1/1963 | Chandler ........................ 328/165 X |
| 3,365,931 | 1/1969 | MacRitchie et al. ................. 73/23.1 |
| 3,497,814 | 2/1970 | Munt .................................... 328/55 |
| 3,698,237 | 10/1972 | Rhodes, Jr. ........................... 73/23.1 |

Primary Examiner—Stanley D. Miller, Jr.
Assistant Examiner—B. P. Davis

[57] ABSTRACT

The resolution of chromatographic peaks is enhanced by removing trailing edges from the peaks. This is accomplished by combining a first signal representative of the chromatographic analyzer output with one or more delayed second signals which are derived from the first signal.

14 Claims, 7 Drawing Figures

CHROMATOGRAPHIC ANALYZER SIGNAL RESOLUTION

Chromatographic analyzers of various types have been developed to perform analyses of fluid mixtures. In general, a sample of the fluid to be analyzed is introduced into a column which contains a packing material that selectively retards passage of the individual constituents of the mixture. A carrier fluid is passed through the column to elute the constituents in succession. The eluted constituents are passed to a detector which measures changes in composition of the column effluent. The detector normally establishes an output electrical signal which comprises a series of peaks when plotted as a function of time.

Most chromatographic peaks are asymmetrical, and frequently this asymmetry or "tailing" decreases resolution to such an extent that the desired precision of analysis is lost. In accordance with this invention, a procedure is provided for enhancing the resolution of chromatographic peaks by removing trailing edges from the peaks. This is accomplished by combining a first signal which is representative of the detector output with one or more delayed second signals which are derived from the first signal. Electrical circuits are provided for carrying out this operation.

In the accompanying drawing, FIGS. 1 to 7 are schematic electrical circuits of embodiments of the apparatus of this invention.

It has been found that actual "tailed" chromatographic peaks can be reproduced quite accurately as a sum of terms involving ideal symmetrical peaks. In mathematical terms, this can be expressed as follows:

$$F(t) = a_0 G(t) + a_1 G(t) * \frac{1}{\tau_1} e^{-\frac{t}{\tau_1}} + a_2 G(t) * \frac{1}{\tau_2} e^{-\frac{t}{\tau_2}} + \ldots \quad (1)$$

$$a_0 + a_1 + a_2 + \ldots = 1 \quad (2)$$

where $F(t)$ is the function representing the actual tailed peak, such as the detector output voltage expressed as a function of time $t$. $G(t)$ is the function representing the symmetrical peak, and the $a$'s are the fractions of the symmetrical peak subject to each delay. Thus, $a_0$ is the fraction subjected to no delay, $a_1$ is the fraction subjected to delay $\tau_1$, etc. The $\tau$'s are first order time constants, and the symbol * represents a convolution.

Although a large number of terms would be required in equation (1) to represent $F(t)$ in terms of $G(t)$ if $G(t)$ were a perfectly symmetrical function, only a few terms, 2 to 4, for example, are generally required to obtain a function $G(t)$ of sufficient accuracy for most practical analyses.

The Laplace transform of equation (1) is $$F(S) = a_0 g(S) + \frac{a_1}{1 + S\tau_1} g(S) + \frac{a_2}{1 + S\tau_2} g(S) + \ldots \quad (3)$$

This equation can be rearranged to the form $$g(S) = \frac{F(S)}{a_0 + \frac{a_1}{1 + S\tau_1} + \frac{a_2}{1 + S\tau_2} + \ldots} \quad (4)$$

Equation (4) is an explicit expression for the transform $g(S)$ of the desired symmetrical peak. This transform is a simple product of the transform $F(S)$ of the observed asymmetrical peak and a transfer function involving empirical constants ($a$'s and $\tau$'s) selected to perform the desired operation. In these equations, $S$ is the Laplace variable.

If two terms are adequate to provide the desired resolution, equation (4) becomes $$g(S) = \frac{(1 + S\tau_1)}{1 + (1 - a_1) S \tau_1} F(S) \quad (5)$$

If three terms should be required, equation (4) becomes $$g(S) = \frac{(1+S\tau_1)(1+S\tau_2)}{[1+(1-a_1)S\tau_1][1+(1-a_2)S\tau_2] - a_1 a_2 S^2 \tau_1 \tau_2} F(S) \quad (6)$$

A second mathematical model has also been found which is capable of describing a real tailed peak in terms of a symmetrical peak. The second model reproduces the real peak by subjecting a symmetrical peak to a series of successive first order delays rather than the parallel delays employed in the first model. The equation for the second model, in Laplace coordinates, is as follows:

$$g(S) = \frac{(1+S\tau_1)(1+S\tau_2)(1+S\tau_3)}{[1+(1-a_1)S\tau_1][1+(1-a_2)S\tau_2][1+(1-a_3)S\tau_3]\ldots} \quad (7)$$

In this model, each of the $a$'s may take on any value between 0 and unity. The sum of the $a$'s need not be unity, as is required in the first model. It can be observed that the two models are identical if the desired resolution can be accomplished by correction for a single delay. The two models are not the same if correction for more than one delay is required, although they may be the same for all practical purposes for a two delay correction if the product of $a_1$ times $a_2$ is much less than 1, as is frequently the case in actual practice.

In both models, the area of the reference peak $G(t)$ is identical to the area of the real peak $F(t)$.

Referring now to the drawing in detail and to FIG. 1 in particular, there is shown a first embodiment of an electrical circuit which is capable of resolving chromatographic peaks in accordance with the foregoing description. The apparatus of FIG. 1 includes a conventional chromatographic analyzer 10, the output signal of which comprises an electrical voltage which varies as a function of time in accordance with the composition of the column effluent. This output signal is applied to a terminal 11 which becomes the input terminal of the circuit to be described. A resistor 12 is connected between terminal 11 and the input of a first operational amplifier 13 which is provided with a feedback resistor 14. The output of amplifier 13 is connected to an output terminal 15, which in turn is connected to a measuring device such as a recorder 16. The output of amplifier 13 is connected by a resistor 18 to the input of a second operational amplifier 19, which is provided with a variable feedback resistor 20. The output of amplifier 19 is connected by a resistor 21 to the input of amplifier 13.

The output of amplifier 13 is also connected by series connected resistors 22 and 23 to the input of a third operational amplifier 24, which is provided with a feedback capacitor 25. A resistor 26 is connected between the output of amplifier 24 and the junction between resistors 22 and 23. The output of amplifier 24 is connected by a resistor 27 to the input of amplifier 19.

Because multiplication by S in Laplace space corresponds to differentiation in the time domain, equations (4) through (7) can be transformed back to the time domain by replacing $S$ with the operator $d/dt$, which will be indicated by the symbol $p$ in the following equations. Equation (5), for example, when transformed back to the time domain, becomes $$G(t) = \frac{1 + \tau_1 p}{1 + (1-a_1)\tau_1 p} F(t) \qquad (8)$$

The apparatus thus far described in FIG. 1 is capable of providing an output in accordance with equation (8). The value of $a_1$ is set by adjustment of resistor 20, and the value of $\tau_1$ is set by the selection of the value of capacitor 25 and adjustment of variable resistor 23. The value of $a_1$ is thus equal to the quotient of resistor 20 divided by resistor 18, and $\tau_1$ is equal to $(2R+R_1)C$, where $R$ is the value of resistor 23, $R_1$ is the value of identical resistors 18 and 22, and $C$ is the value of capacitor 25. In one specific embodiment, resistors 12, 14, 18, 21, 22 and 26 can be 10K ohms each. Resistor 20 can be 0–10K ohms, and resistor 23 can be 10K–1M ohms. Capacitor 25 can be 10 microfarads.

If a second delay is required to provide the desired resolution of the chromatographic peak, the apparatus thus far described in FIG. 1 can be expanded by connecting a second delay unit corresponding to the one previously described, wherein corresponding elements are designated by like primed reference numerals, in parallel. Similarly, even more delay units can be added in parallel if further resolution is desired.

Figure 2:
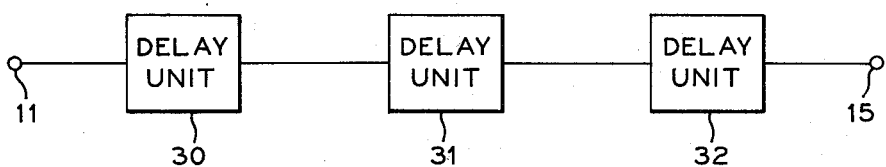

A second procedure to incorporate corrections for more than one first order delay involves connecting several individual delay units of the type shown in FIG. 1 in series. This is illustrated in FIG. 2 wherein three delay units 30, 31 and 32 are connected in series between terminals 11 and 15. It is to be understood that each of these delay units comprises the circuit illustrated in FIG. 1 between terminals 11 and 15 (elements 12, 13, 14 and 18 through 27), but does not include the second delay unit of FIG. 1 which is illustrated by the primed reference numerals.

Figure 3:
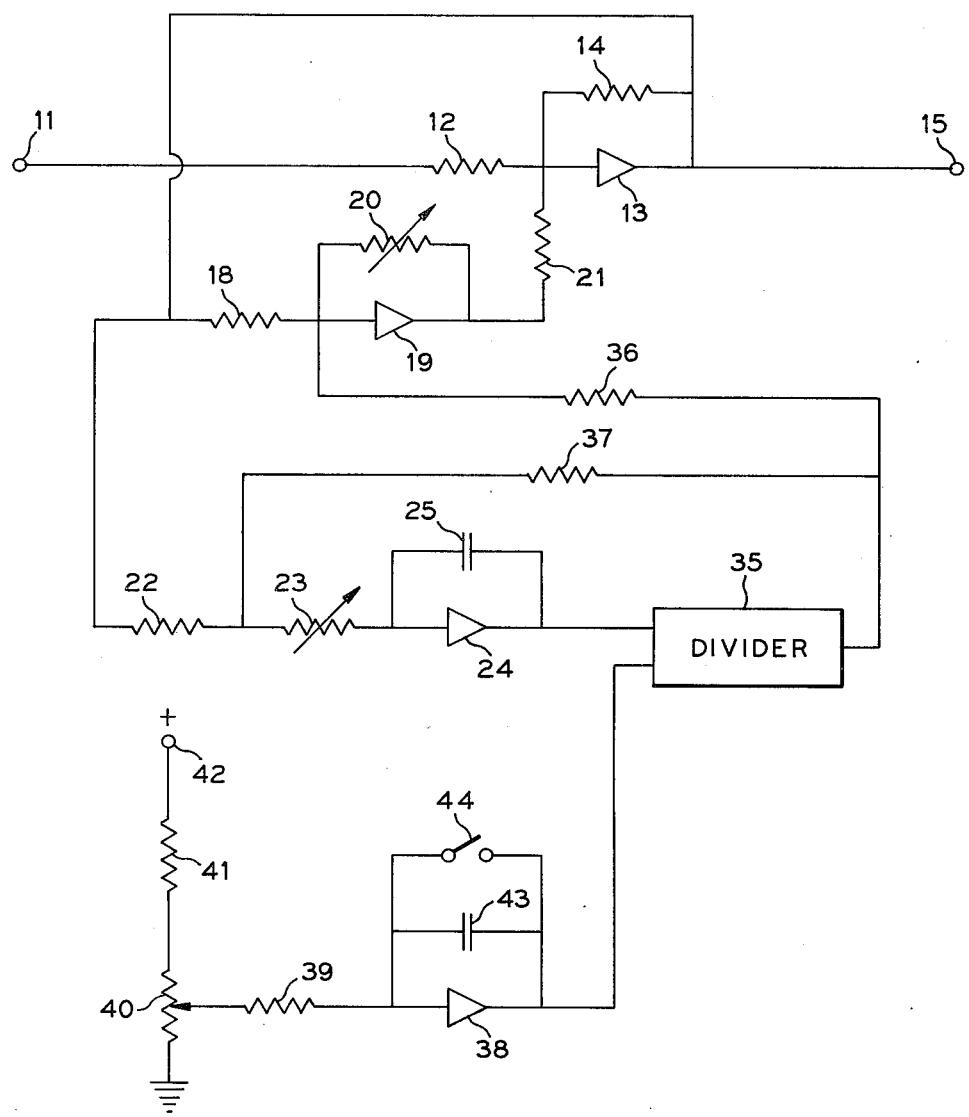

The apparatus thus far described is quite satisfactory for detailing a single chromatographic peak. However, additional circuit elements are required if several successive peaks are to be de-tailed. This is due to the fact that the $\tau$ value required for the operation are different for each chromatographic peak. However, it has been found that the appropriate $\tau$ values for each peak in a multicomponent chromatograph are proportional to the elution times of the individual peaks. The a values, on the other hand, are substantially identical for all peaks. An embodiment of apparatus which can be employed with successive peaks is illustrated in FIG. 3. This apparatus includes amplifiers 19 and 24 and associated circuit elements which correspond to those illustrated in FIG. 1. In the circuit of FIG. 3, the output of amplifier 24 is applied to the first input terminal of a signal dividing circuit 35. The output of circuit 35 is connected by resistor 36 to the input of amplifier 19. A resistor 37 is connected between the output of divider 35 and the junction between resistors 22 and 23. The second input of divider 35 is connected to the output of a fourth operational amplifier 38. The input of amplifier 38 is connected by a resistor 39 to the contactor of a potentiometer 40. One end terminal of potentiometer 40 is connected to ground, and the second end terminal is connected by a resistor 41 to a terminal 42 which is maintained at a positive potential. Amplifier 38 is provided with a feedback capacitor 43. A switch 44 is connected in parallel with capacitor 43.

In the circuit of FIG. 3, a negative-going ramp signal, initiated at zero time in the chromatograph, is generated by amplifier 38. This zero time corresponds to the time of sample injection into the analyzer and is established by opening switch 44 at such time. Circuit 35 divides the output signal from amplifier 24 by the ramp output signal from amplifier 38. The resulting quotient is applied to summing amplifier 19. This produces the desired effect of increasing the effective time constant in the feedback loop of amplifier 24 in direct proportion of elapsed time. The value of $\tau$, employing the circuit of FIG. 3, is given by $$\tau = e_t \frac{(2R + R_1)C_1}{10R_2C_2} t \qquad (9)$$

if the divider has the transfer function $e_y = -10e_z/e_x$. In these relationships, $e_t$ is the voltage at the contactor of potentiometer 40, $R$ is the value of resistor 23, $R_1$ is the value of resistor 37, $C_1$ is the value of capacitor 25, $R_2$ is the value of resistor 39, $e_y$ is the voltage at the output of divider 35, $e_z$ is the voltage at the output of amplifier 24, and $e_x$ is the voltage at the output of amplifier 38. The desired proportionality constant between $\tau$ and $t$ is set by selection of the values of resistors 23 and 39, capacitors 25 and 43 and the input voltage to amplifier 38 which is adjusted by potentiometer 40. It should be evident that the additional circuit elements of FIG. 3 can also be incorporated in the parallel delay unit circuit of FIG. 1 or the series delay unit circuit of FIG. 2. In such applications, it is not necessary to have separate ramp generators for each section. A single ramp generator can provide the voltage to the second input of the divider circuit of each section. In conjunction with the specific embodiment previously described, resistors 22, 36, 37 and potentiometer 40 can be 10K ohms each. Resistor 23 can be 1M ohms, and resistor 39 can be 50K–1M ohms. Capacitors 25 and 43 can be 10 microfarads each.

Figure 4:
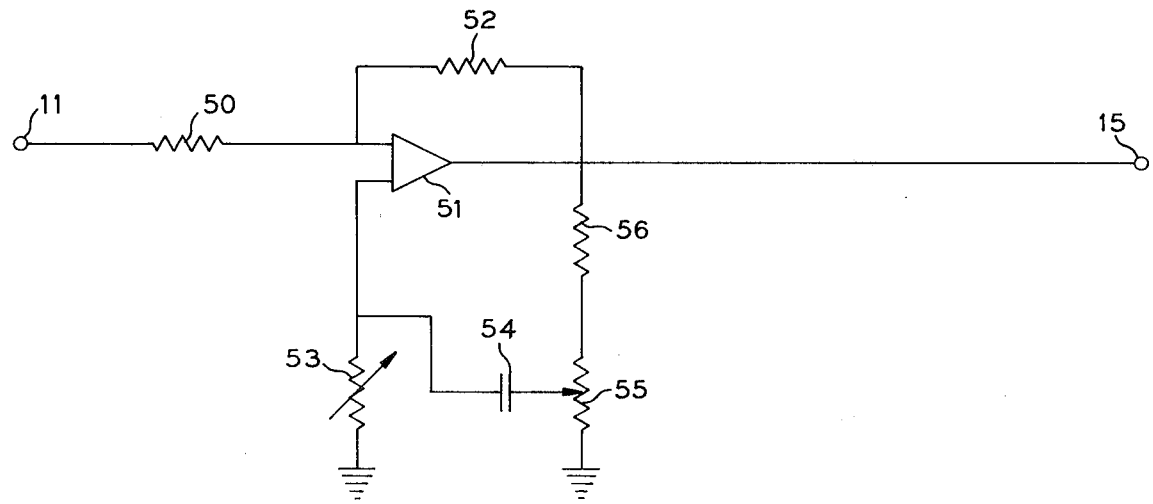

A simplified version of the circuit of FIG. 1 incorporating a single delay unit is illustrated in FIG. 4. Terminal 11 is connected by a resistor 50 to the first input of a differential amplifier 51. The output of amplifier 51 is connected to terminal 15. A resistor 52 is connected between the output of amplifier 51 and the first input terminal thereof. A variable resistor 53 is connected between the second input of amplifier 51 and ground. A capacitor 54 is connected between the second input of amplifier 51 and the contactor of a potentiometer 55. One end terminal of potentiometer 55 is connected to ground, and the second end terminal is connected by a resistor 56 to the output of amplifier 51. A plurality of delay units of the type illustrated in FIG. 4 can be connected in series as shown in FIG. 2. In one specific embodiment, resistors 50 and 52 can be 10K ohms each. Resistor 56 and potentiometer 55 can be 2K ohms each. Resistor 53 can be 50K–1M ohms. Capacitor 54 can be 10 microfarads.

Figure 5:
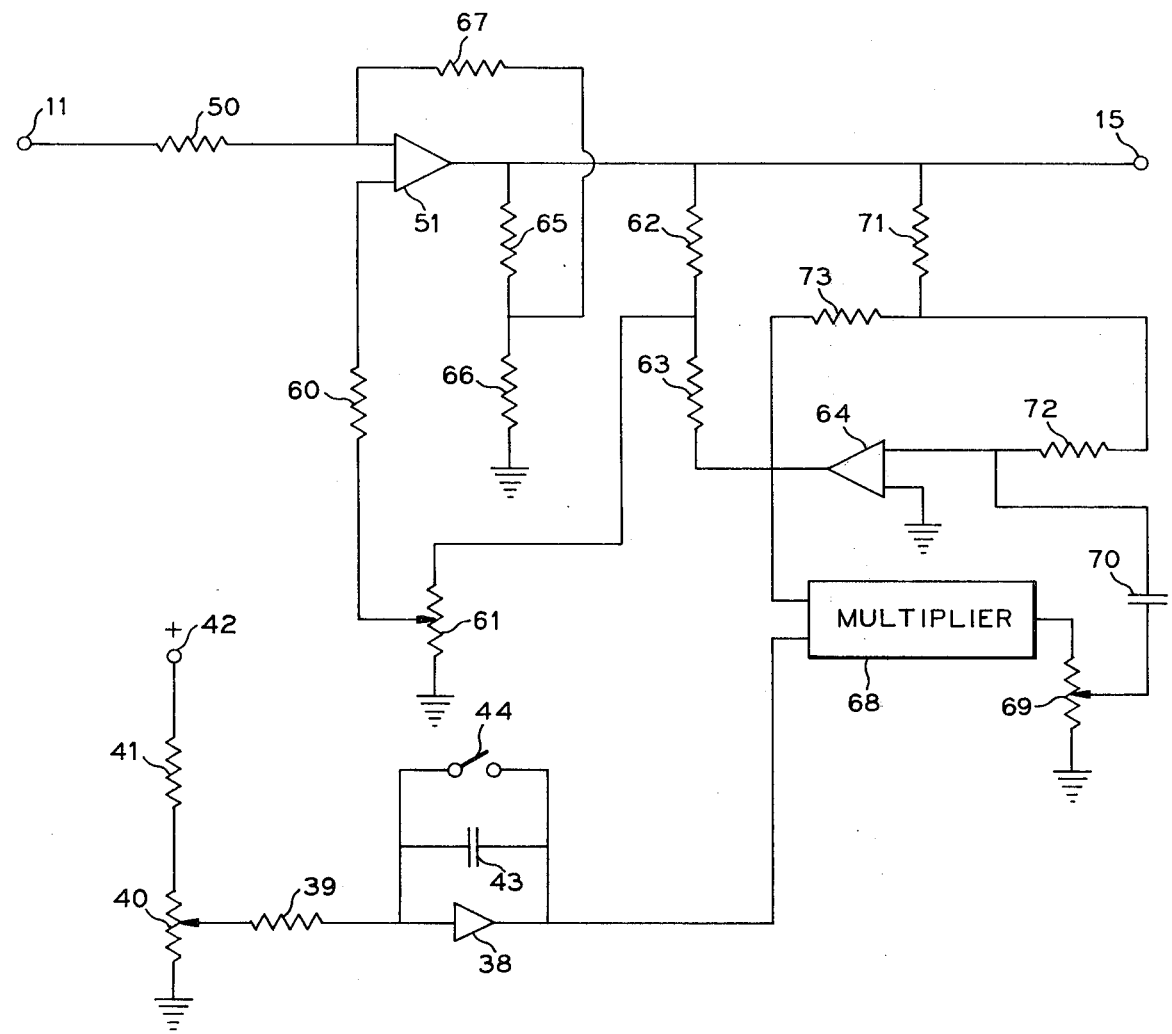

Another embodiment of the apparatus of this invention is illustrated in FIG. 5. The circuit of FIG. 5 incorporates features of the circuits of FIGS. 3 and 4. The second input of amplifier 51 is connected by a resistor 60 to the contactor of a potentiometer 61. The first end terminal of potentiometer 61 is connected to ground, and the second end terminal is connected to the junction between resistors 62 and 63. Resistors 62 and 63 are connected in series relationship between the output of amplifier 51 and the output of an amplifier 64. The output of amplifier 51 is connected to ground by series connected resistors 65 and 66. A feedback resistor 67 is connected between the junction between resistors 65 and 66 and the first input of amplifier 51.

The output of amplifier 64 is connected to the first input terminal of a multiplier circuit 68. The output of amplifier 38 is connected to the second input of multiplier 68. The output of multiplier 68 is connected to the first end terminal of a potentiometer 69, the second end terminal of which is connected to ground. The contactor of potentiometer 69 is connected by a capacitor 70 to the first input of amplifier 64, the second input of which is connected to ground. The output of amplifier 51 is connected by series connected resistors 71 and 72 to the first input of amplifier 64. The junction between resistors 71 and 72 is connected by resistor 73 to the output of amplifier 64.

In one specific embodiment of the circuit of FIG. 5, resistors 71, 73 and potentiometers 61, 40 can be 10K ohms each. Resistors 62, 63 and 41 can be 5K ohms each. Resistors 39 and 72 can be 50K–1M ohms each. Resistors 50, 67, 65, 66 and 60 can be 1M, 500K, 250K, 500K and 470K ohms, respectively. Capacitors 43 and 70 can be 10 microfarads each.

Figure 6:
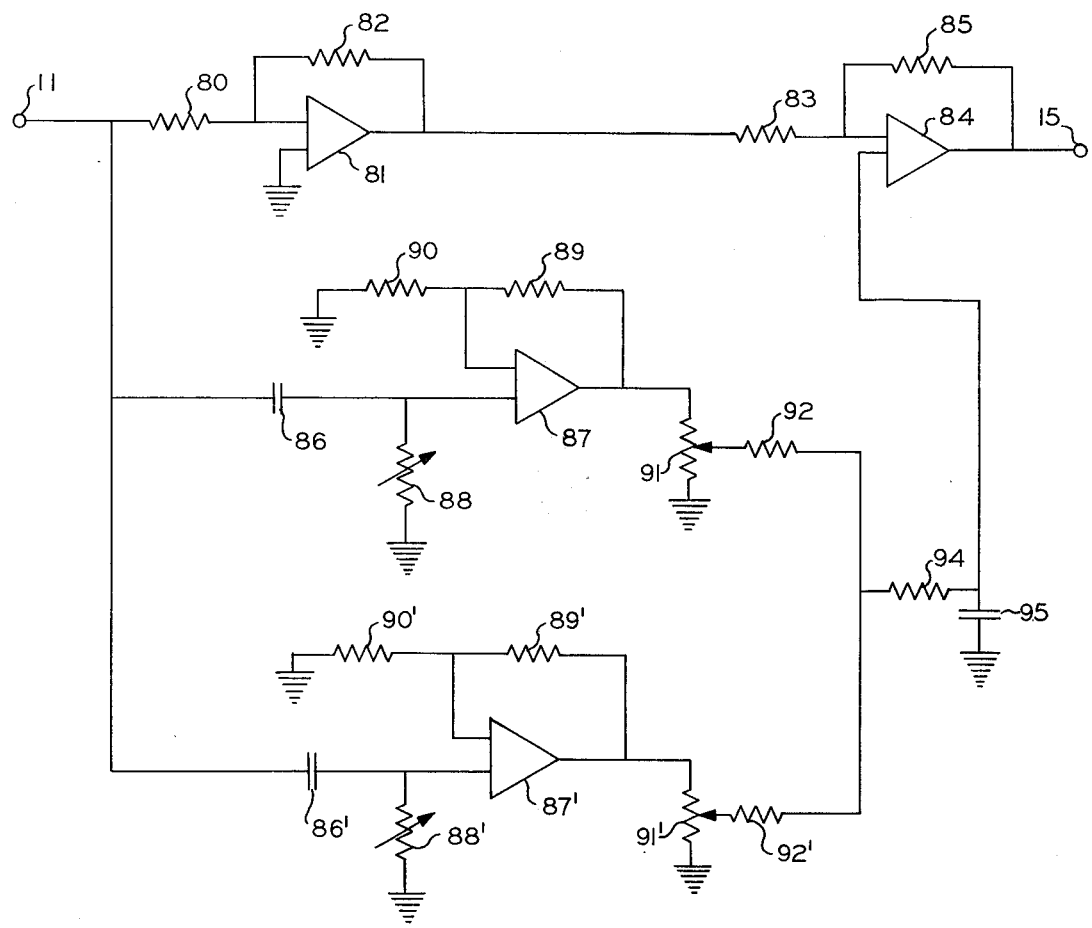

A modification of the circuit of FIG. 1 is illustrated in FIG. 6. Input terminal 11 is connected by a resistor 80 to the first input of an operational amplifier 81, the second input of which is connected to ground. Amplifier 81 is provided with a feedback resistor 82. The output of amplifier 81 is connected by a resistor 83 to the first input of a summing amplifier 84, the output of which is connected to terminal 15. Amplifier 84 is provided with a feedback resistor 85.

Input terminal 11 is also connected by a capacitor 86 to the second input of an operational amplifier 87. This second input is connected to ground by a variable resistor 88. A feedback resistor 89 is connected between the output and the first input of amplifier 87. A resistor 90 is connected between this first input and ground. The output of amplifier 87 is connected to the first end terminal of a potentiometer 91, the second end terminal of which is connected to ground. Amplifier 87 and the circuit elements associated therewith constitute a delay unit wherein capacitor 86 and resistor 88 form a differentiating circuit. The circuit of FIG. 6 is provided with a similar second delay unit which is indicated by like primed reference numerals.

The contactors of potentiometers 91 and 91' are connected by respective resistors 92 and 92' to the first terminal of a resistor 94. The second terminal of resistor 94 is connected to the second input of amplifier 84. A capacitor 95 is connected between this second input and ground. Thus, the two delayed signals are summed with the original signal transmitted through amplifier 81. In one specific embodiment, resistors 80, 82, 83, 85, 89, 90, 89', 90', 92, 92', 94 and potentiometers 91 and 91' can be 10K ohms each. Potentiometers 88 and 88' can be 1M ohms each. Capacitors 86, 86' and 95 can be 10 microfarads each. Resistor 94 and capacitor 95 form a filter circuit.

Figure 7:
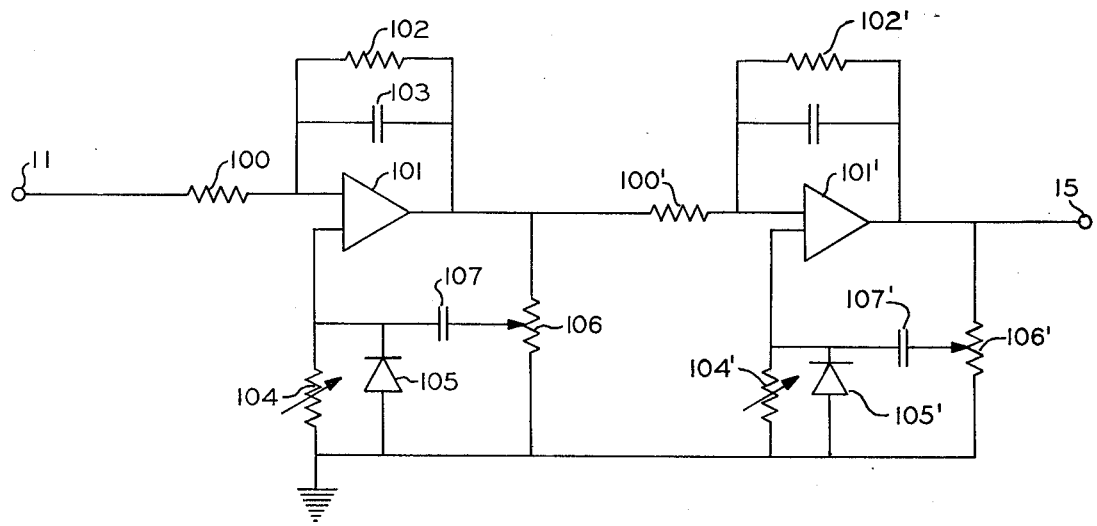

Still another embodiment of this invention which incorporates two delay units in series is illustrated in FIG. 7. Input terminal 11 is connected by a resistor 100 to the first input of an amplifier 101. Amplifier 101 is provided with a feedback resistor 102 having a capacitor 103 connected in parallel therewith. The second input of amplifier 101 is connected by a variable resistor 104 to ground. A rectifier 105 is connected in parallel with resistor 104. The output of amplifier 101 is connected to the first end terminal of a potentiometer 106, the second end terminal of which is connected to ground. A capacitor 107 is connected between the contactor of potentiometer 106 and the second input of amplifier 101.

The circuit of FIG. 7 includes a second unit corresponding to the one previously described wherein similar elements are designated by like primed reference numerals. The output of amplifier 101' is connected to terminal 15. In one specific embodiment, resistors 100, 102, 100' and 102' and potentiometers 106 and 106' can be 10K ohms each. Variable resistors 104 and 104' can be 1M ohms each. Capacitors 103 and 103' can be 0.01 microfarad each, capacitor 107 can be 15 microfarads, and capacitor 107' can be 10 microfarads.

While this invention has been described in conjunction with presently preferred embodiments, it should be evident that it is not limited thereto.

What is claimed is:

1. In a chromatographic analyzer in which an output signal is established which varies in amplitude in accordance with changes in composition of the effluent from a separation column therein; the improvement comprising apparatus to remove trailing edges from peaks in the output signal comprising means responsive to the output signal to establish a delayed signal derived from the output signal, and means to sum the delayed signal and the output signal to establish a composite signal from which at least a part of the trailing edge of a peak has been removed.

2. The apparatus of claim 1, further comprising means to establish at least one additional delayed signal derived from the output signal and delayed a different amount than the first-mentioned delayed signal, and means to sum the at least one additional delayed signal with the output signal.

3. The apparatus of claim 2 wherein the means to establish the first-mentioned delayed signal and the means to establish the at least one additional delayed signal are connected in series relationship.

4. The apparatus of claim 2 wherein the means to establish the first-mentioned delayed signal and the means to establish the at least one additional delayed signal are connected in parallel relationship.

5. The apparatus of claim 1 wherein said means to establish a delayed signal comprises a differentiating circuit and an operational amplifier connected in series relationship, the input of said differentiating circuit being said output signal, and said means to sum receives the output of said operational amplifier and said output signal.

6. The apparatus of claim 5, further comprising a second differentiating circuit and a second operational amplifier connected in series relationship with one another and in parallel with the first-mentioned differentiating circuit and operational amplifier.

7. The apparatus of claim 1 wherein said means to establish a delayed signal comprises an operational amplifier having first and second inputs and an output, said first input receiving said output signal, a feedback resistor connected between said output and said first input, a capacitor connected between said output and said second input, and a second resistor connected between said second input and a point of reference potential.

8. The apparatus of claim 7, further comprising a second operational amplifier having first and second inputs and an output, the output of the first-mentioned operational amplifier being connected to the first input of said second operational amplifier, a second feedback resistor connected between the output and first input of said second operational amplifier, and a fourth resistor connected between the second input of said second operational amplifier and said point of reference potential.

9. The apparatus of claim 1 wherein said means to establish a delayed signal comprises an operational amplifier having a feedback capacitor, means including a first resistor to apply a signal to the input of said operational amplifier representative of the output of said means to sum, and means to apply the output of said operational amplifier to the input of said means to sum.

10. The apparatus of claim 9, further comprising a signal summing means having the output thereof connected to the input of said means to sum, and means connecting the output of said means to sum and the output of said operational amplifier to the input of said summing means.

11. The apparatus of claim 10, further comprising a signal dividing means having two inputs and an output, means connecting the output of said operational amplifier to the first input of said dividing means, a ramp signal generator, means connecting the output of said ramp signal generator to the second input of said dividing means, said dividing means establishing an output signal representative of the quotient of the signal applied to the first input divided by the signal applied to the second input, and means connecting the output of said dividing means to the input of said signal summing means.

12. The apparatus of claim 1 wherein said means to establish a delayed signal comprises an operational amplifier, a signal multiplier having first and second inputs and an output, a ramp signal generator, means connecting the output of said ramp signal generator to the first input of said multiplier, means connecting the output of said operational amplifier to the second input of said multiplier, and means to apply said composite signal to the input of said operational amplifier, the output of said operational amplifier constituting said delayed signal.

13. The apparatus of claim 12, further comprising a second operational amplifier having first and second inputs and an output, feedback means connected between the output and the first input of said second operational amplifier, the first input of said second operational amplifier being adapted to receive said output signal, and means connecting an output signal from the first-mentioned operational amplifier to the second input of said second operational amplifier.

14. Analysis apparatus comprising a chromatographic analyzer to establish an output signal which varies in amplitude in accordance with changes in composition of the effluent from a separation column in the analyzer; means responsive to the output signal from said analyzer to establish a delayed signal derived from said output signal; and means to sum the delayed signal and the output signal to establish a composite signal from which at least a part of the trailing edge of a peak in the output signal has been removed.

* * * * *